United States Patent [19]

Fullmer

[11] Patent Number: 4,855,923
[45] Date of Patent: Aug. 8, 1989

[54] PARTS ASSEMBLY USING SIGNATURE ANALYSIS

[75] Inventor: David M. Fullmer, Ann Arbor, Mich.

[73] Assignee: Xerox Corporation, Stamford, Conn.

[21] Appl. No.: 141,235

[22] Filed: Jan. 6, 1988

[51] Int. Cl.$^4$ .................. G06F 15/46; G06F 15/36
[52] U.S. Cl. ............................... 364/468; 364/558; 364/554; 73/862.53
[58] Field of Search ............... 364/468, 513, 550, 563, 364/558, 476, 487, 554; 901/3, 9, 30, 33, 34; 73/862.04, 862.51, 862.64, 862.53, 862.67, 862.23

[56] References Cited

U.S. PATENT DOCUMENTS

| | | | |
|---|---|---|---|
| 3,984,006 | 10/1976 | Takeyasu et al. | 214/1 BB |
| 4,150,360 | 4/1979 | Kopp et al. | 340/146.3 |
| 4,213,036 | 7/1980 | Kopp et al. | 235/92 |
| 4,275,986 | 6/1981 | Engelberger et al. | 901/3 |
| 4,548,066 | 10/1985 | Martinez et al. | 364/563 |
| 4,593,367 | 6/1986 | Slack et al. | 364/513 |
| 4,621,332 | 11/1986 | Sugimoto et al. | 364/513 |
| 4,639,996 | 2/1987 | Fullmer | 29/407 |
| 4,704,909 | 11/1987 | Grahn et al. | 73/862.04 |
| 4,706,505 | 11/1987 | King | 73/862.64 |
| 4,750,131 | 6/1988 | Martinez | 73/862.53 |

*Primary Examiner*—Jerry Smith
*Assistant Examiner*—Paul Gordon
*Attorney, Agent, or Firm*—H. Fleischer; J. E. Beck; R. Zibelli

[57] ABSTRACT

A method of assembling parts in which, before actual assembly of the parts, the forces associated with a good assembly of parts and the forces associated with a faulty assembly of parts are identified to train a pattern of recognition signature analysis system. During assembly, the forces required to actually assemble the parts are measured and a determination is made by the system as to whether these forces are associated with a good assembly or a faulty assembly to determine if the assembled part should be accepted or rejected.

5 Claims, 19 Drawing Sheets

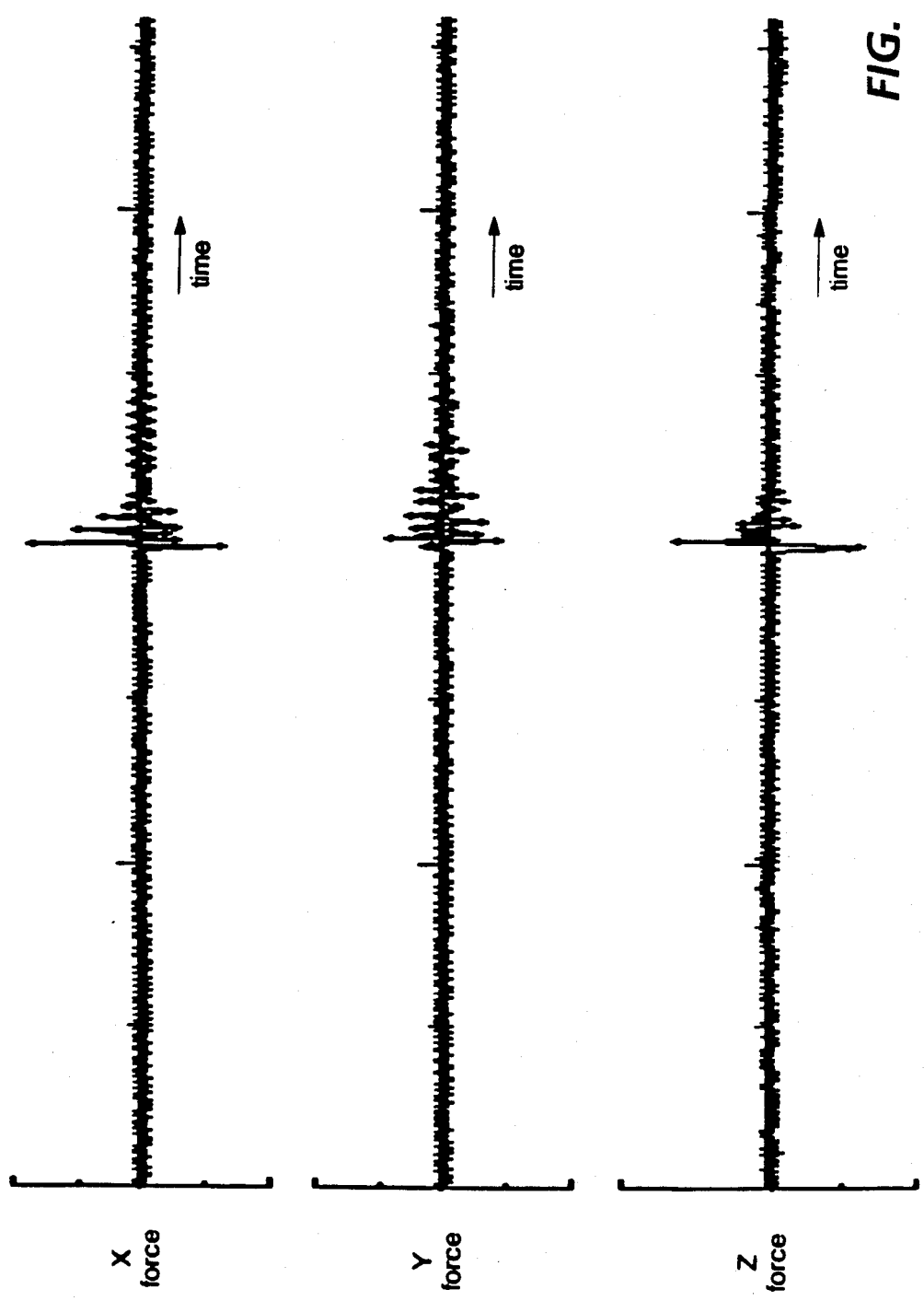

PARTS ASSEMBLY USING SIGNATURE ANALYSIS

This invention relates generally to a method of assembling parts, and more particularly concerns the automatic assembly of parts by an assembly robot which classifies the assembled parts as a good or a faulty assembly.

Robots installed in flexible assembly systems are instrumented with sensors to insure that assembly processes are in control. The sensing systems are often custom designed for each assembly task and must be discarded when a different product is being assembled. As more sensors are integrated into a flexible assembly system over its' lifetime, the total system cost continues to increase. Assembly cost can be reduced by eliminating the redesigning of the the sensing system for each new assembly job. Thus, if an approach could be devised to reuse the physical components of a sensor system, the recurrent integration costs of hard tooled sensors could be eliminated. One such approach applies the technique of signature analysis to the robotic assembly forces. In signature analysis, a repeating process is instrumented. The measured waveform of the repeated process repeats and serves as a characteristic signature of the process. If the process changes, the signature waveform will also change. Thus, signature analysis is a technique where an analysis of the process signatures is used to determine the process from which the waveforms were created.

Extensive work in robotic assembly techniques has previously been done by the Charles Stark Draper Laboratory, Inc. of Cambridge, Mass. Their work led to the mathematical investigation of the expected three dimensional forces incurred during peg insertion. They also developed a mechanically compliant structure to provide small corrective motions in response to error forces during the peg and hole assembly. The Remote Center Compliance, or RCC, was developed for this purpose. The RCC allows a robot to perform close tolerance insertions or even press fits in less than 0.2 seconds, Nevins, J. L. and Whitney, D. E., "Assembly Research", Automatica, Volume 16, Pages 595-613, (1980), Pergamon Press Ltd.; Gustavson, R. E., "A Theory for the Three-Dimensional Mating of Chamfered Cylindrical Parts", Charles Stark Draper Laboratory, Inc., Cambridge, Mass.; Seltzer, D. S., "Tactile Sensory Feedback for Difficult Robot Tasks", Robot VI Conference Proceedings, Mar. 1-4, 1982, Charles Stark Draper Laboratory, Inc., Cambridge, Mass. Along with the RCC device, some robots have built in compliance. These robots are known as Selective Compliant Assembly Robot Arms or SCARA, Polleto, A., Xerox Automation Institute Robotics/Automation Volume 1, Chapter 1, June, 1984. Compliance is permitted on the horizontal plane leaving the insertion axis stiff. In addition to the purely mechanical compliance, researchers have also developed a six axis force sensor. The sensor is mounted at the robot wrist and enables insertion of parts by analyzing the forces and determining the correct robot movements. The use of a force sensor to analyze insertion forces is an example of adaptive control. In adaptive control, forces acting on the sensor are fed back to the robot controller causing a modification of the preprogrammed path according to the applied forces. Adaptive control techniques have been used in grinding, deburring and assembly. This technique has become the principle alternative to visions systems to provide sensory data, Mason, M. and Salisbury, J., "Robot Hands and the Mechanics of Manipulation, "MIT Press, Cambridge, Massachusetts, Pages 55-64, (1985); Nevins, J. L., "Adaptive Control, Learning and Cost Effective Sensor Systems for Robotics or Advanced Automation Systems", Final Report April, 1985-Sept. 30, 1986, Charles Stark Draper Laboratory, Inc., Cambridge, Mass.; Breen, J., "Force Sensing or Vision: Weighing the Advantages", Robotics Today, Society of Manufacturing Engineers, Pages 35-36, April, 1985. Force sensors have also been applied to robots for monitoring operations to determine if a process is occurring normally without adaptive control. Many of these applications have set maximum and minimum force threshold limits which are not to be exceeded. Presently, assembly force signature analysis is limited to where the forces are tested against threshold limits.

Signature analysis has been applied to many industrial operations. For example, in paper mills, this technique has been used to detect bearing and blade deterioration, electrical defects, and roll deterioration, Thorp, B., Benjamin, A., and Barasch, M., "Maintaining the Paper Mill Through Vibration Analysis", PIMA, Pages 47-54, February, 1984. Signature analysis has also been applied to detect vibrations and loose parts in nuclear power plants, Albrecht, R. W., Crowe, R. D., and McGuire, J. J., "The Fast-Data System Fully Automatic Stochastic Technology for Data Acquisition Transmission and Analysis", Department of Nuclear Engineering, University of Washington, Seattle, Wash., Nuclear Power Plant Control and Instrumentation, Pages 397-413, 1978. In France, signature analysis was used for a robotic asparagus picker, Baylow, P., El Hadj Amor, B., and Bousseau, G., "Automatic Recognition of Moving Objects and its Application to a Robot for Picking Asparagus", Laboratoire d'Automatique, de Reconnaissance des Formes et de Robotique Agricole de L'Ecole Nationale Superieure d'Electronique et de Radioelectricite de Bordeaux 351 cours de la Liberation, 33405 Talence Cedex, France, Proceedings of SPIE, Volume 397, Pages 234-239, 1983. Other applications of signature analysis have occurred in electronic circuit testing, optical character recognition, nerve cell activity, nuclear explosion detection, inertial guidance systems, and radar aircraft identification, Murray, A. F., Denyer, P. B., and Renshaw, D., "Self-Testing in Bit Serial VLSI Parts: High Coverage at Low Cost", Wolfson Microelectronics Institute, Department of Electrical Engineering, University of Edinburgh, Mayfield Road, Edinburgh EH 3JL, IEEE, 1983, International Test Conference, Paper 11.1, Pages 260-268; Fukushima, K. and Miyake, S., "Neocognitron: Self-Organizing Network Capable of Position-Invariant Recognition of Patterns", Fifth International Conference on Pattern Recognition, IEEE Cat. No. 80CH 1499-3, Pages 459-461, 1980; Misheievich, D. J., "On-Line Real-Time Digital Computer Separation of Extracellular Neuroelectric Signals", Transaction on Bio-Medical Engineering, Volume BME-28, No. 12, Pages 804-812, December, 1981; Hall, C. F., "The Analysis of Random Aperiodic Signals Using an Adaptive Classifier", Naecon 1971 Record, Air Force Institute of Technology, Wright-Patterson AFB, OH 45433, Pages 274-278; Hostetler, L. D., "A Kalman Approach to Continuous Aiding of Inertial Navigation Systems Using Terrain Signatures" Sandia Laboratories, Albuquerque, N.

Mex., Milwaukee Symposium on Automatic Computation and Control, Rashba, S., "Aircraft Identification Based on Pattern Recognition of FM Emission Specta", Bradley University Department of EE/EET, Morgan Hall, Peoria, Ill. 61625, Modelling and Simulation Proceedings of the 14th Annual Pittsburgh Conference, Volume 14, 277-286, 1983. In many applications of signature analysis, a generalized algorithm does not perform as well as one which is specialized or intuitive, Nagy, G., "State of the Art in Pattern Recognition", Proceedings of the IEEE, Volume 56, No. 5, Pages 836-864, 1968; Bernstein, M. I., "Computer Recognition of On-Line, Hand-Written Characters", Memo RM-3758, Rand Corp., Santa Monica, Calif., October, 1964; Groner, G. F., "Real-Time Recognition of Hand Printed Symbols", IEEE Pattern Recognition Workshop, Puerto Rico, October, 1966; "Through Testing: Right the First Time", Product Engineering, September, 1979; Thompson, T., "Ford's V-6 Engine Assembly and Quality Assurance System", Assembly Engineering, Pages 34-39, October 1981; U.S. Pat. No. 4,639,996 issued Feb. 3, 1987 to Fullmer. Heuristic methods such as these are largely responsible for most of the signature analysis algorithms reported to date.

It may be difficult to develop a heuristic classification scheme for waveforms where little is known about the signature of the process. Under these circumstances, alternative techniques are used. One such alternative is to collect signatures from the instrumented process and extract features of interest. These features are grouped and classified using a suitable classification algorithm. One method for determining group membership of some particular sample is linear classification. Linear classification consists of drawing a line between the groups. The point in question is classified by determining which side of the line it is on with the aid of a weighting vector. The simplest method of computing the weighting vector is to use a correlation technique. Maximum likelihood classification determines the class which is most likely to contain the point in question. This classification uses concepts of Baysian logic to determine group membership. Alternatively a trainable categorizer may be used. In a trainable categorizer, the weight vector is updated throughout the process and the distribution of the sample does not have to be normal, Kanal, L., "Evaluation of a Class of Pattern-Recognition Networks", Biological Prototypes and Synthetic Systems, New York: Plenum, Pages 261-270, 1962; Bryan, J. S., "Experiments in Adaptive Pattern Recognition", Preceedings, 1963 Bionics Symposium, (Preprint), USAF; Konheim, A. G., "Linear and Nonlinear Methods in Pattern Classification", IBM Journal of Research and Development, July, 1964; Casey, R. G., "An Experimental Comparison of Several Design Algorithms Used in Pattern Recognition", Report RC 1500, Watson Research Center, IBM Corp., Yorktown Heights, N.Y., November, 1965. In some instances, a line to separate the data points into groups is not the best solution. For Gaussian distributions, an optimal separating surface is a hyperquadric, Cooper, P. W., "Hyperplanes, Hyperspheres, and Hyperquadrics as Decision Boundaries, "Computer and Information Science, Washington, D.C., Spartan, Pages 111-139, 1964. The nearest neighbor decision algorithm assigns an unknown data point to the nearest group. This classification scheme has an error approximately twice that of an optimal Baysian classifier, Cover, P. W., and Hart, P., "The Nearest Neighbor Decision Rule", International Symposium on Decision Theory, 1966; Cover, T. M., and Hart, P., "Nearest Neighbor Pattern Classification", IEEE Transactions on Information Theory, Volume IT-13, Pages 21-27, January, 1967. If a training set is small, and/or the data points drift with time, an adaptive or trainable categorizer may be needed. These algorithms are known as tracking, nonsupervised learning, self or error-correcting behavior, or adaptive algorithms. Some applications of these classification schemes have been voice recognition and interpreting Morse code signals, Gold, B., "Machine Recognition of Hand-Sent Morse Code", IRE Transactions on Information Theory, Volume IT-5, Pages 17-24, March 1959; Selfridge, O. G., and Neiser, U., "Pattern Recognition by Machine", Scientific American, Pages 60-68. August, 1960. Cluster analysis assigns waveforms into groups or clusters that are suggested by the data within the waveform and are not previously defined. Waveforms identified in a defined cluster tend to be similar to each other in some manner, and waveforms in different clusters tend to be correspondingly dissimilar. Noise and data errors may cause large errors in clustering classification schemes. Algorithms have been developed that clearly separate and identify clusters regardless of their shape, Bonner, R. E. "A logical Pattern Recognition Program", IBM Journal of Research and Development, Volume 6, Pages 353-359, July, 1962; Abrahm, C., "Evaluation of Clusters on the Basis of Random Graph Theory", IBM Research Memo, IBM Corp., Yorktown Heights, N.Y., November, 1962. Occasionally, the dimensionality of the data for classifications is so high that the application of classification algorithms becomes extremely tedious. The amount of data may be limited by using some form of feature extraction. Various classification and parts assembly approaches have been devised. The following disclosures appear to be relevant:

U.S.-A No. 3,984,006, Patentee: Takeyasu et al., Issued: Oct. 5, 1976.

U.S.-A No. 4,150,360, Patentee: Kopp et al., Issued Apr. 17, 1979.

U.S.-A No. 4,213,036, Patentee: Kopp et al., Issued July 15, 1980.

U.S.-A No. 4,593,367, Patentee: Slack et al., Issued: June 3, 1986.

U.S.-A No. 4,621,332, Patentee: Sugimoto et al., Issued: Nov. 4, 1986.

U.S.-A No. 4,639,996, Patentee: Fullmer, Issued: Feb. 3, 1987.

The relevant portions of the foregoing patents may be summarized as follows:

U.S.-A No. 3,984,006 discloses an automatic assembly control system for inserting an object into a hole. When the object is detected in a restricted condition, a search motion in the direction perpendicular to the direction of insertion, following an adequate search pattern, is initiated by a positioning mechanism. The inserting operation is resumed after the position at which the restriction is released has been detected.

U.S.-A No. 4,150,360 and U.S.-A No. 4,213,036 describe a method and apparatus for classifying biological cells. A statistical technique is used to investigate the discriminating capability of the various features. The statistical technique includes Baysian decision theory for a multivariate Gaussian process and the concept of diversions as a measure of the performance of the specific feature or group of features.

U.S.-A No. 4,593,367 discloses a probabilistic learning element relating to training or learning systems capable of defining their own internal processing in response to information descriptive of system performance. Sequences of received objects are correlated with information relating to previously learned states in order to assign probabilities to possible next states in the sequence of recognized states.

U.S.-A No. 4,621,332 describes a method and apparatus for controlling a robot wherein a force signal is calculated by detecting a force applied to a hand of a robot based on a force signal relating to a force applied to the hand, a position signal, a velocity signal, a spring constant, a mass coefficient and a viscosity coefficient.

U.S.-A No. 4,639,996 discloses an apparatus which automatically attaches a threaded fastener to an article. The apparatus positions the threaded fastener in contact with the article and applies a torque thereon. A signal is generated indicating the torque level. The signal is compared to preset limits. Different preset torque limits are set for tapping threads in a hole in the article and securing the fastener therein.

In accordance with one aspect of the present invention, there is provided a method of assembling parts. Before actual assembly of the parts, the forces associated with a good assembly of parts and the forces associated with a faulty assembly of parts are identified. During actual assembly of the parts, the forces are measured. The measured forces are compared to the identified forces to determine if the measured force is associated with a good assembly or a faulty assembly.

Other aspects of the present invention will become apparent as the following description proceeds and upon reference to the drawings, in which:

FIG. 8 shows the x, y, and z force waveforms when there is no part in the end effector gripper of the FIG. 2 robot;

While the present invention will hereinafter be described in connection with a preferred embodiment, it will be understood that it is not intended to limit the invention to that embodiment. On the contrary, it is intended to cover all alternatives, modifications, and equivalents, as may be included within the spirit and scope of the invention as defined by the appended claims.

Figure 1:
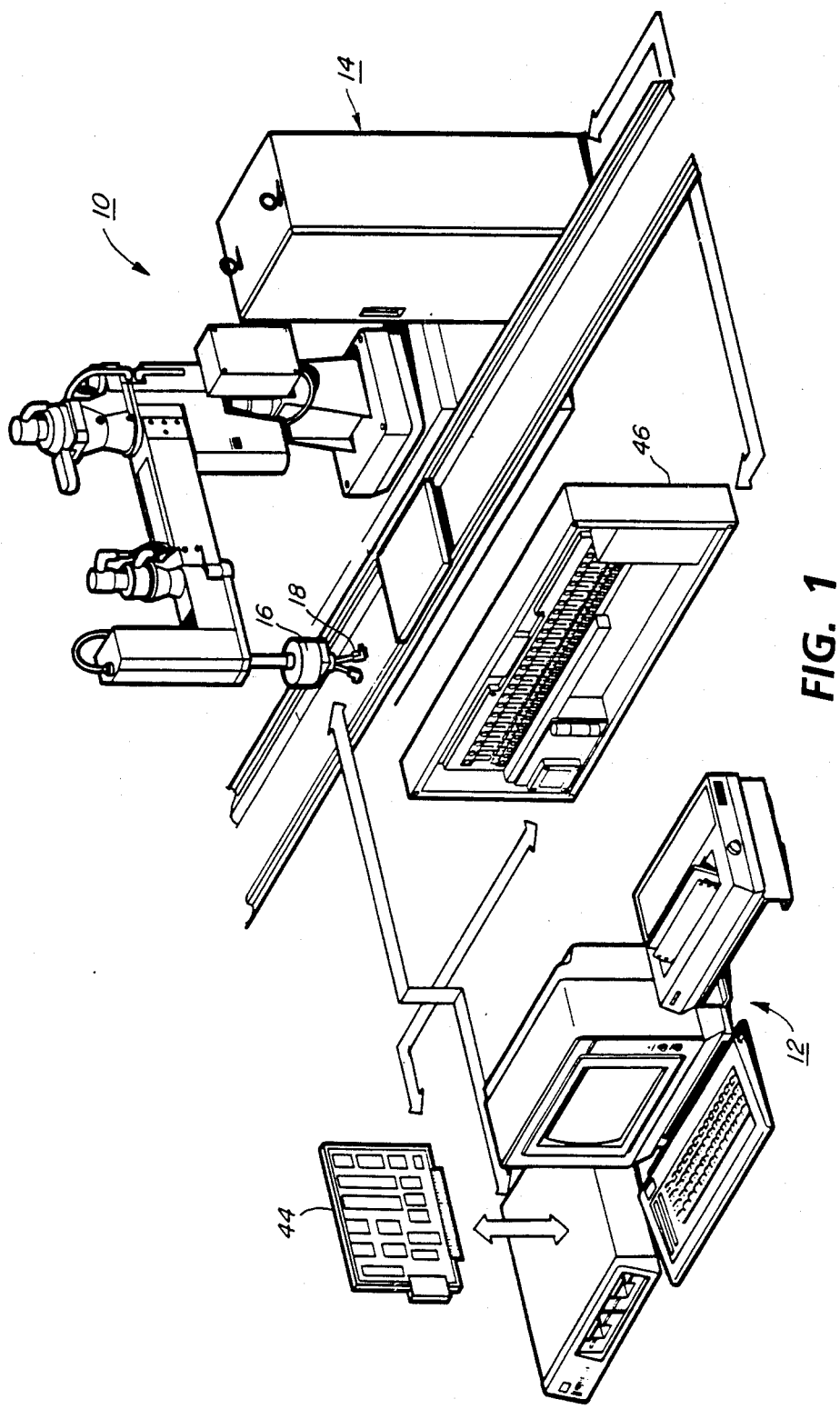
FIG. 1 is a schematic perspective view depicting the various elements of the apparatus for automatically assembling a part and determining whether the assembly was good or faulty.

For a general understanding of the features of the present invention, reference is made to the drawings. In the drawings, like reference numerals have been used throughout to identify identical elements. FIG. 1 schematically depicts the various components of the apparatus for assembling parts incorporating the features of the present invention therein. It will become evident from the following discussion that the method of parts assembly of the present invention may be employed in a wide variety of devices and is not specifically limited in its application to the particular embodiment depicted herein.

While many classification algorithms are available, the linear classifier selected was the "maximum likelihood" type. The algorithm is based on small sample theory enabling the use of a smaller learning set, Cooley, W. W. and Lohnes, P. R. "Multivariate Data Analysis", John Wiley & Sons, Inc., Chapters 8–10, 1971. The waveform classification is Sons, Inc., Chapters 8–10, 1971. The waveform classification is accomplished by first obtaining a training set of extracted features and then defining each different type of insertion as a group. As the groups are defined in this manner, a "flexible" waveform classifier is created. The classification procedure assumes that the data are multivariate and normally distributed. The technique can be visualized by imagining an m-dimensional Euclidean description space D. A point $X \in D$ is defined by a vector of m components, $(x_1, x_2, \ldots, x_m)$. The components of X are the extracted features from an insertion waveform. Upon plotting these vectors, a clustering of feature vector end points becomes apparent. During the training phase, the operator identifies the names of each of the clusters as the condition which occurred during the insertion. These conditions might be, (1) loss of part, (2) part inserted backwards, etc. Upon completion of the training, unknown insertion vectors are mapped into this hyper-space. Identification or classification is achieved by determining the closest cluster to the vector end point. The clusters are very dense in the region known as the group centroid, m, and thin out in all directions. The thinning is not constant in all directions due to the variance and covariances between the features. This is given by the group dispersion, D, in the following equation. The clusters are hyper-ellipsoidal in this hyper-space. A hyper-ellipsoidal can be loosely thought of as a surface that when intersected by a plane produces an ellipse. Each point on a hyper-ellipsoidal can be thought of as having the same probability of occurrence relative to its group centroid. The Baysian classification of a vector that defines the probability hypothesis, $H_j$, given the feature vector, X, to a group can be expressed as:

$$Pr(H_j|X_i) i=1,2 \ldots N \text{ and } j=1,2 \ldots g,$$

where:

N = number of feature variables making up the vector for each group, j,
g = total number of groups, and
X = waveform vector.

A distance function acting within this space is used to determine the probability of membership of an unknown vector with the different groups. This distance function can be modified to incorporate apriori probabilities of the different classifications. In this application, however, it is assumed that any insertion vector has an equal probability of occurrence. Therefore, the probability of hypothesis $H_j$, given feature vector, X, can be found by:

$$P_{ij} = q_j \left[ \frac{N_j}{(N_j+1)} \right]^{1/2p} \left[ \frac{(N-g+1)}{(N_j-p-g+1)} \right]$$

-continued $$\left[ 1 + \frac{N_j(X_i - m_i)^T D^{-1}(X_i - m_j)}{(N_j+1)(N-g)} \right]^{-1/2(N-g+1)}$$

where:

$$m_j = \frac{1}{N} \sum_{i=1}^{N_j} X_{ji},$$

$$D = \left[ \sum_{i=1}^{N} X_i X_i^T \right] - mm^T$$

$q_j$ = priori probabilities vector for each group $j=1/g$,
m = centroid location for each group,
$D^{-1}$ = inverse of group dispersion Variance-Covariance matrix,
i = feature number, and
j = group number.

Figure 2:
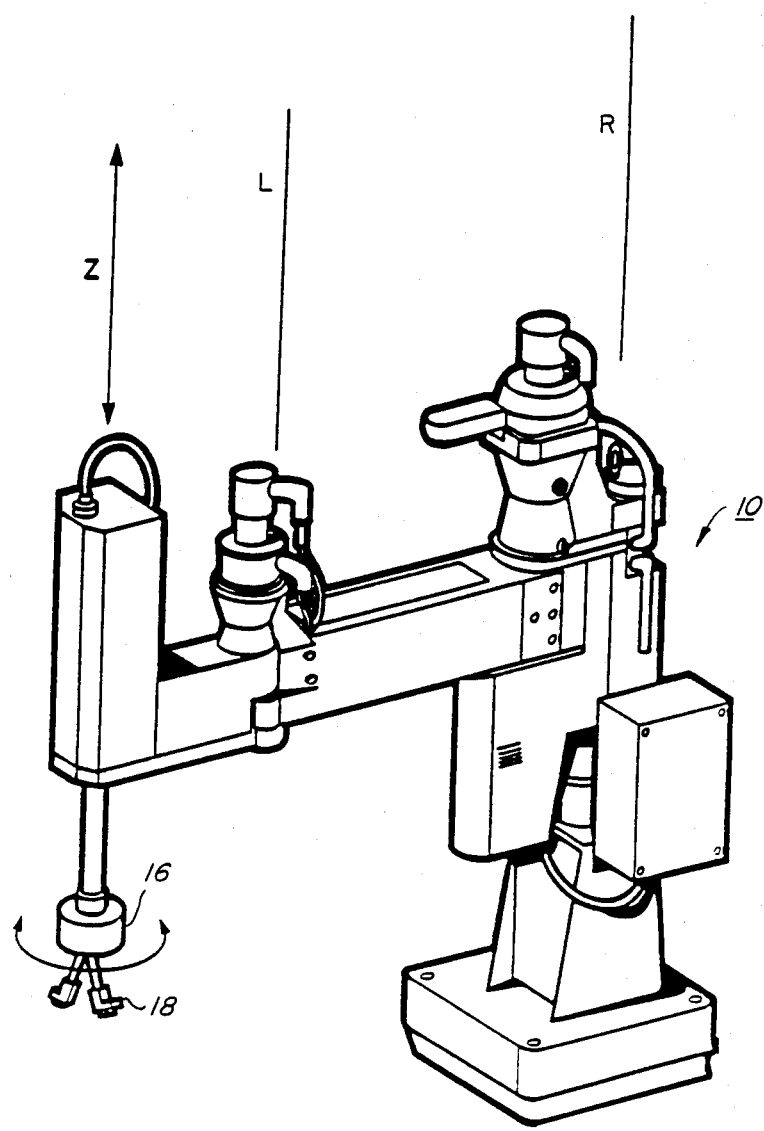
FIG. 2 is a schematic perspective view showing the assembly robot used in the FIG. 1 apparatus.

Referring to FIG. 1 of the drawings, the parts assembly system developed to implement the foregoing algorithm includes a robot, indicated generally by the reference numeral 10, and a computer, indicated generally by the reference numeral 12. A controller, indicated generally by the reference numeral 14, houses all of the servo amplifiers and logic cards necessary to provide power and signals to robot 10. It is programmed off-line by computer 12 Robot 10 is made by the IBM Corporation as Model No. 7545. This assembly robot is shown in greater detail in FIG. 2. This assembly robot has four degrees of motion: rotation about the L and R axes, a z-stroke (up and down), and roll of wrist 16. Computer 12 is made by IBM Corp. as the model PC. The computer has 512k of memory with two 350k double sided disk drives. It is configured with one communication port and a color graphics adapter. Computer 10 is equipped with four languages: Basic, Fortran, Pascal and AML. AML is the robot machine language. Basic language was used because of its built-in ability to buffer the RS232 port used to communicate with the force wrist 16 secured to the arm of robot 10. Fortran was used for 3-dimensional plotting of data. Turbo-Pascal, developed by Borland International, was used for the remaining software. Turbo-Pascal's execution speed is very fast, and the program sizes are extremely small. This is very important since the computer disk size is limited to approximately 350K bytes. In addition, the Turbo Graphics Tool Box developed by the Borland International is used for the graphic routines.

A pneumatic gripper 18 is mounted on wrist 16. Upon actuation of an air valve, the gripper closes. As the air is removed from the gripper, it is opened by the action of a spring. Fingers on the gripper enable the gripper to pick up the part being assembled.

Figure 3:
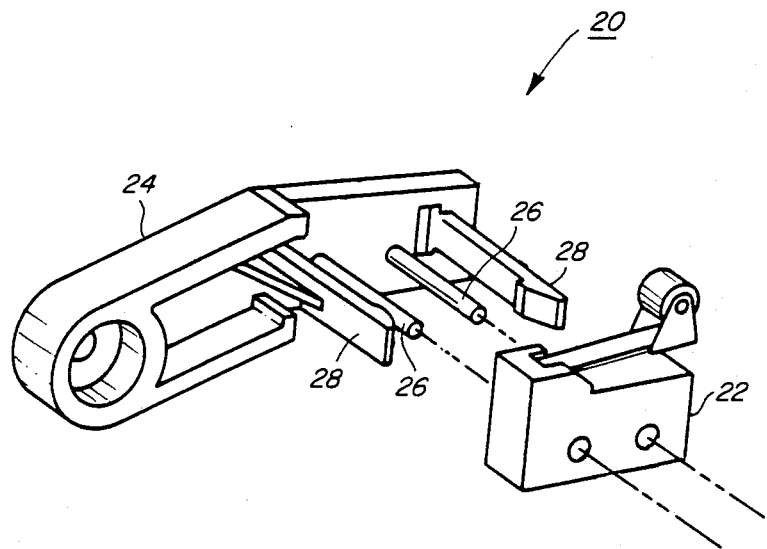
FIG. 3 is a schematic perspective view illustrating a part being assembled by the FIG. 1 apparatus.
Figure 4:
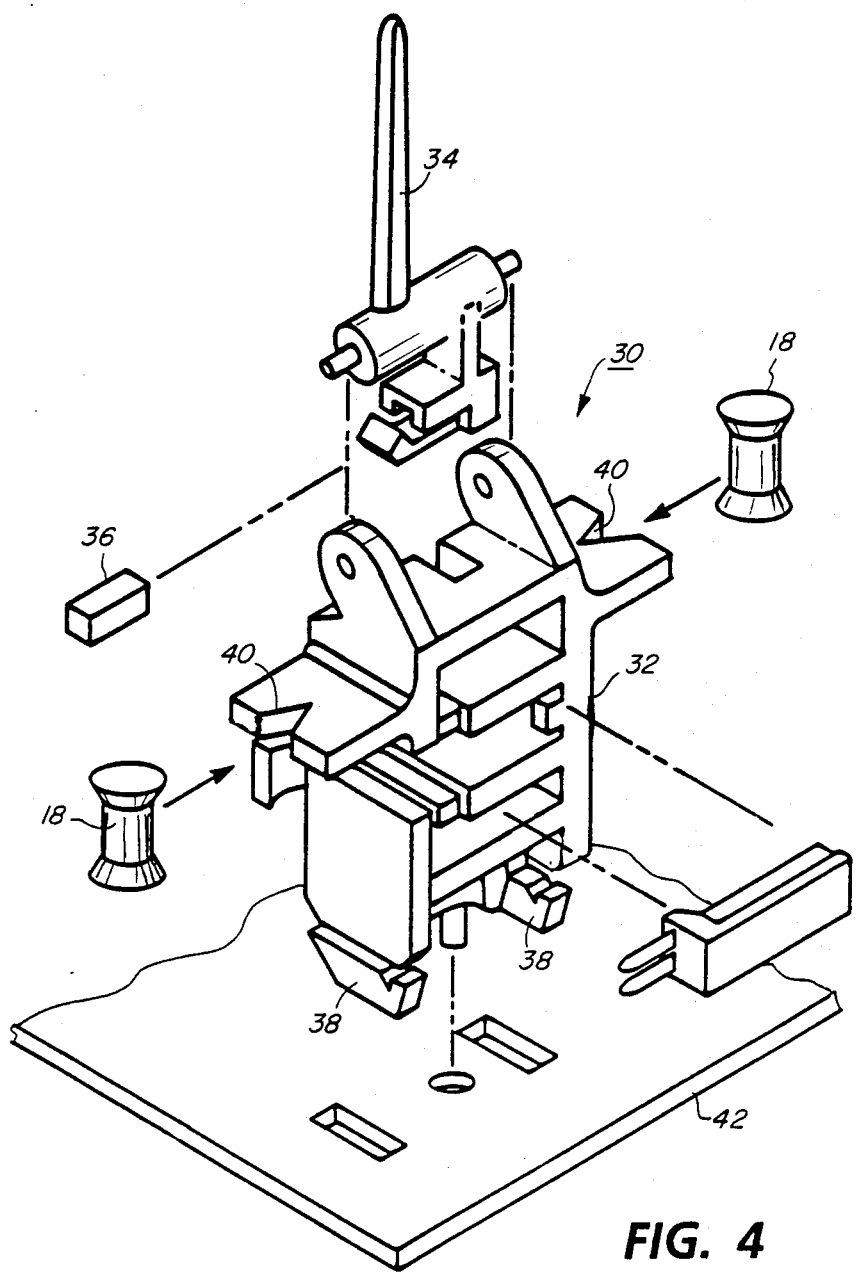
FIG. 4 is a schematic perspective view showing further details of a part being assembled by the FIG. 1 apparatus.

As competition increases among companies, products are being designed both to reduce assembly labor and the number of parts. A major part reduction can be obtained if screws are eliminated by designing the parts to be self fastening. Parts can be made self-fastening by taking advantage of the snap action of certain plastics or metals. Snapping parts together is advantageous in terms of assembly time, "Final Gains", Yankee Conveyor, March-April, 1985, Volume 3, No. 2, Page 50, The Yankee Group, 89 Broad Street, Boston, Mass. 02110. FIG. 3 depicts an exemplary part, indicated generally by the reference numeral 20, being assembled. Part 20 includes a switch 22 adapted to be mounted on a bracket 24. Bracket 24 has pins 26 for aligning switch 22 with bracket 24. Locking tabs 28 secure switch 22 in place on bracket 24. Traditional robotic instrumentation has often been inadequate for monitoring this type of fastening. Traditionally, limit switches have been used to provide the sensor input to a robot to inform it if processes were completed correctly. For example, did the snap action occur normally? Was the part broken or missing some features? Was the part upside down? Was a wrong, but similar part inserted? Any of these situations may occur and should be protected against. A snap-in switch, indicated generally by the reference numeral 30, was assembled by the method and apparatus of the present invention. FIG. 4 depicts switch 30.

Figure 5:
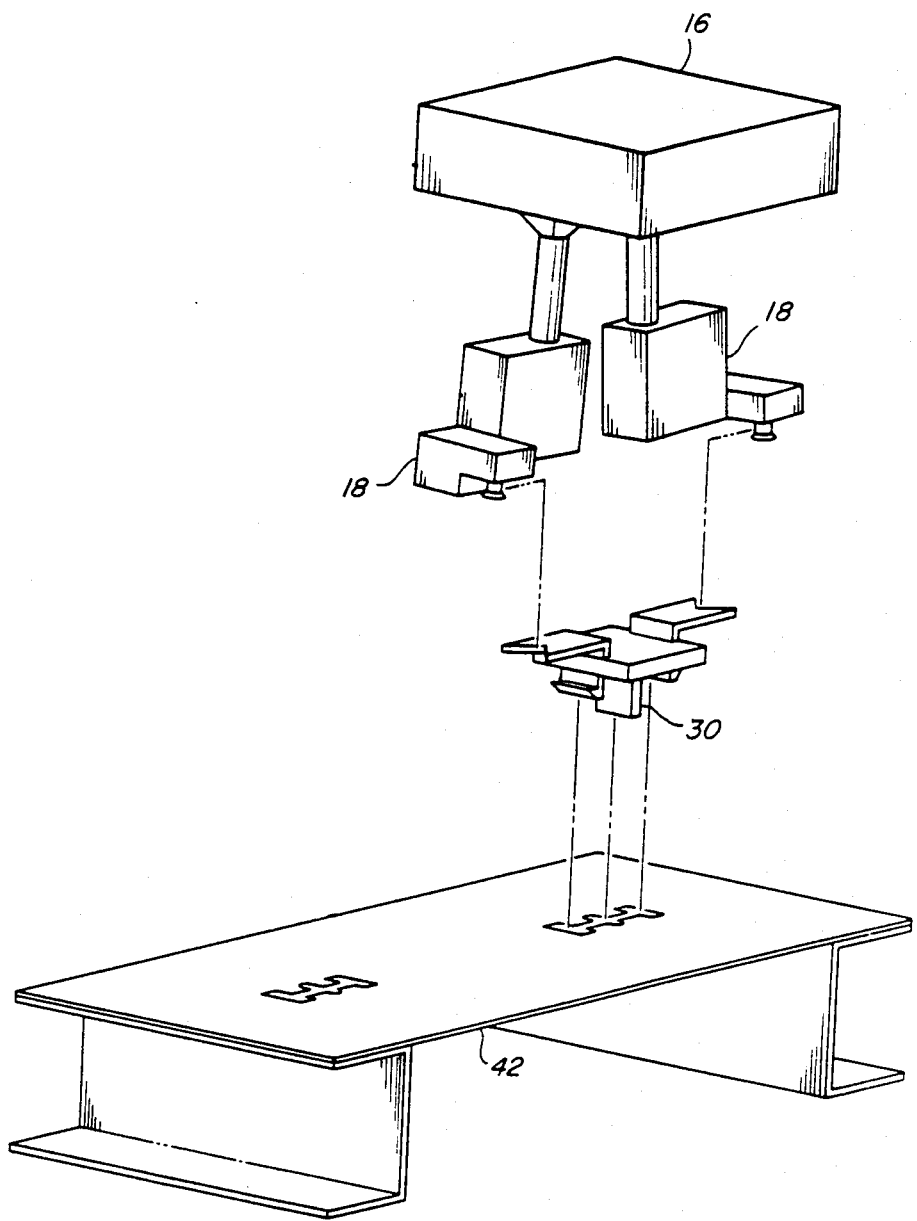
FIG. 5 is a schematic perspective view depicting further details of the assembling of a part by the FIG. 1 apparatus.

As shown in FIG. 4, switch 30 includes a main body 32, a paper flag 34, and a magnet 36. Magnet 36 is used, during switch operation in a copier, to signal a sensor that a copy sheet is present at the switch. The snap feature is obtained by two opposing legs 38. Gripper fingers 18 engage notches 40 for positioning switch 30 for assembly with frame 42. FIG. 5 shows switch 30 secured by gripper fingers 18 extending from force wrist 16. The robot arm is maneuvering switch 30 to assemble it on frame 42.

With continued reference to FIG. 1, force wrist 16, is installed between the robot tool plate and the gripper 18. The wrist provides six channels of force data: forces and moments acting along the x, y and z axis. The wrist is composed of electrically excited strain gauges and a microprocessor which transforms the strain information into the six force and moment values. It includes an RS232 communication port for data transmission. A suitable force wrist is made by the Barry Wright Corporation of Watertown, Mass.

To synchronize data collection, the robot controller 14 sends a trigger signal through an isolation board 46 to computer 12 to identify when part assembly is beginning. This signal comes from the robot controller as a digital signal from a 24V Opto module. An interface card 44, installed in the computer 12, reads this trigger from the controller 14 and provides a signal to the computer data bus where it can be read by a program. By way of example, isolation board 46 may be an Opto 22 PB24 board and interface card 44 an Opto AC 5 card. Both the isolation board and interface card are made by OPTO22, Huntington Beach, Calif.

The operation of the system consists of two phases, learning and classification. The first phase in the operation of the system is to collect the data using a program called "Wristcom". Wrist 16 is oriented on robot 10 such that the x-axis of the sensor is in line with the conveyor direction of motion, the y-axis perpendicular to the conveyor, and the z-axis in the vertical direction with positive being upwards. These coordinate directions are the default selection by the wrist upon power-up. The wrist power supply is a 120 Volt AC power supply, and the RS232 connector is connected to the asychronous communication adapter within computer 12. The adapter and wrist communication protocals are software-programmable.

Forces are obtained from the force sensor as a function of time. The sensor provides force information at a steady frequency. Minor variations in the frequency of transmission can be caused by sending start and stop transmission bits due to the computer getting overrun with data. A transmission rate of 9600 baud was used to achieve a near constant transmission.

Before the Wristcom program can operate, wrist 16 must be initialized. Initialization, which sets up the operating parameters of the sensor, is accomplished by operating a public domain modem program called "PC-Talk". The PC-talk program uses 9600 baud, eight data bits, and no parity. With these parameters set on the computer, a carriage return is sent to the sensor. The sensor has an auto-communication detection system which detects the transmission speed of a carriage return sent to it after an initial power up. At this point, the sensor is now using the proper communication protocal. The sensor has several parameters which have to be specified. One parameter defines the coordinate system for calculating and reporting the forces. It can be defined at the tool tip, for example, or anywhere else in space. The coordinate system is defined at the tool mounting point which is the default coordinate system.

The communication technique selected is known as "Packed Output Format." At the 9600 baud maximum reception rate of the computer, the wrist will provide an output at either 120 Hz or 60 Hz. The two frequencies are determined by the amount of data transmitted. If only forces are transmitted, the sampling rate is 120 Hz. If both forces and moments are transmitted, the sampling rate is 60 Hz. Since robot moves at 144 mm/sec, at its slowest speed, at a 120 Hz sampling rate, the force sensor will output data every 0.0458 inches (1.16 mm). As the deflection of the snap feature of this particular switch is overcome in 0.20 inches (measured on the insertion axis) the deflection would be plotted by 4 to 5 data points. This is an extremely course measurement of the snap deflection. However, a visual review of the plots indicates the different waveforms to be classified are significantly different suggesting that this communication speed should be sufficient. Therefore, to obtain the fastest sampling rate, only three force measurements are transmitted.

Before the sensor is requested to send force information, a reset of the bias command "RB" is issued. This, in effect, considers the present readings of the gripper 18 on the sensor to be zero force. This is useful in nulling out the effects of gripper weights, and sensor warm-up characteristics. As error conditions occur, the sensor intersperses error messages in the data stream. Error condition reporting is turned off to simplify data translation from packed format to numerical data at the computer. To disable the error reporting, the command inhibit threshold "IT" and Inhibit Limits "IL" are issued. The sensor has a threshold rate maximum limit. This is useful for detecting forces which are changing too quickly. The limit routine will indicate if forces have exceeded predefined levels. After these commands are issued, the sensor is instructed to Enable Output "EO". At this command the sensor will output a continuous stream of forces occurring at the sensor. The PC-Talk program can now be stopped, and the WRIST-COM program run.

The WRISTCOM program assumes that the trigger signal is connected. This is done by connecting a 10 volt supply and a load in series with the ODC5 output Opto module in controller 14. An IDC5 input module is then connected across the load to detect the signal. The IDC5 module is plugged into the isolation board 46. A ribbon cable is connected to isolation board 46 and interface card 44 installed in one of the slots of computer 12. The jumpers on the card are installed and set to the proper address to match that of the WRISTCOM program. Once WRISTCOM is executing, the robot application program can be executed. The robot program must set the trigger output high when WRISTCOM is to begin sampling the data and low when the sampling is to stop.

After the WRISTCOM program has finished, the data needs to be converted from packed data format to real numbers. The algorithm consists of scanning the data file until a double zero synchronizing bit is found upon which the following eight bytes are defined as a status byte (2 bytes), and the LSB and MSB of the forces along the x, y and z axis (6 bytes). This cycle repeats sixteen times until the next synchronizing pulse is received. The program which converts the packed data to real values is entitled "CONVERT". After the values have been converted, the forces can be divided into those forces which characterize a good assembly and those forces which indicate potentially faulty assemblies.

Figure 6:
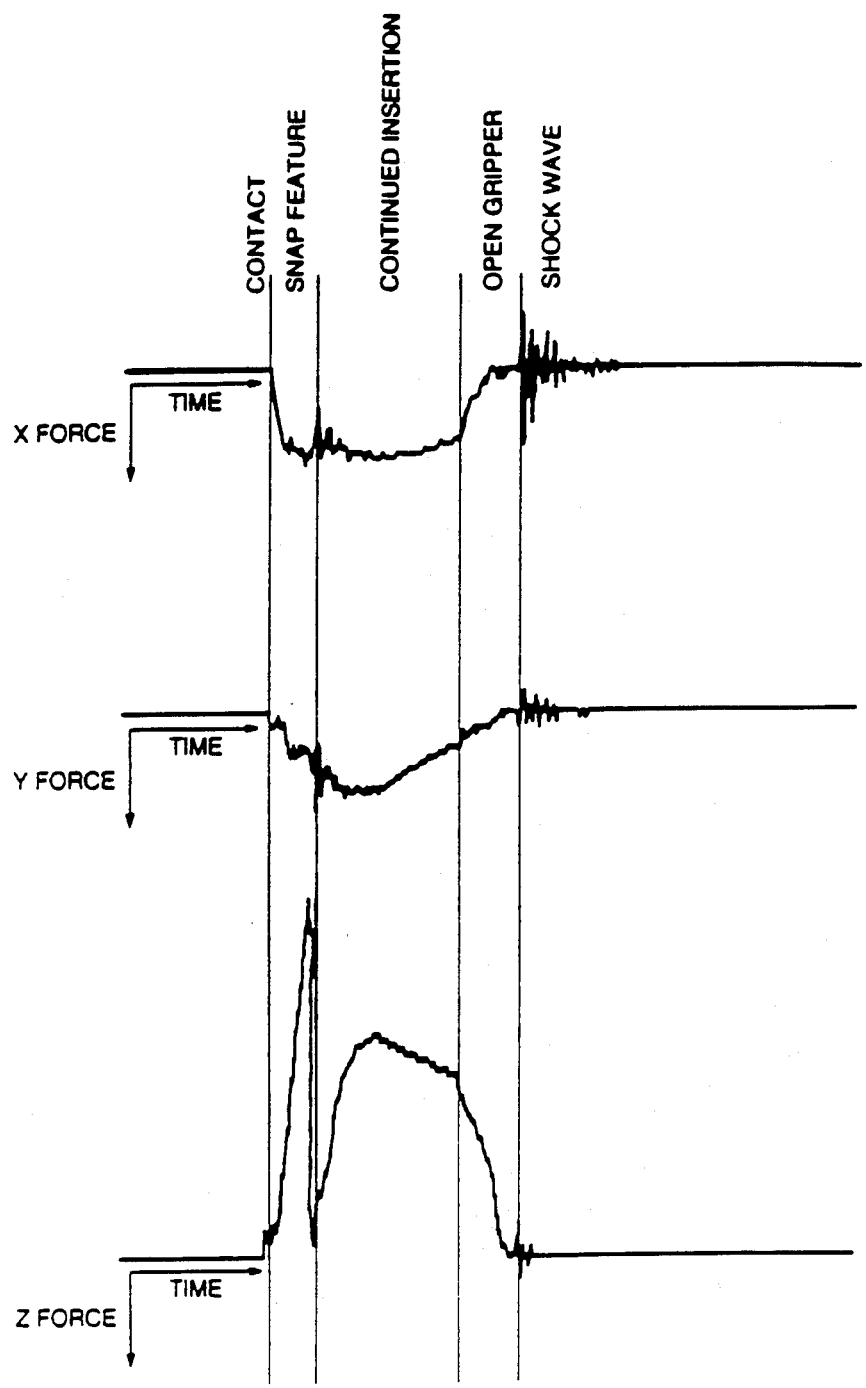
FIG. 6 illustrates the forces acting along the x, y, and z axes of the sensor during a successful assembly of the part.
Figure 7A:
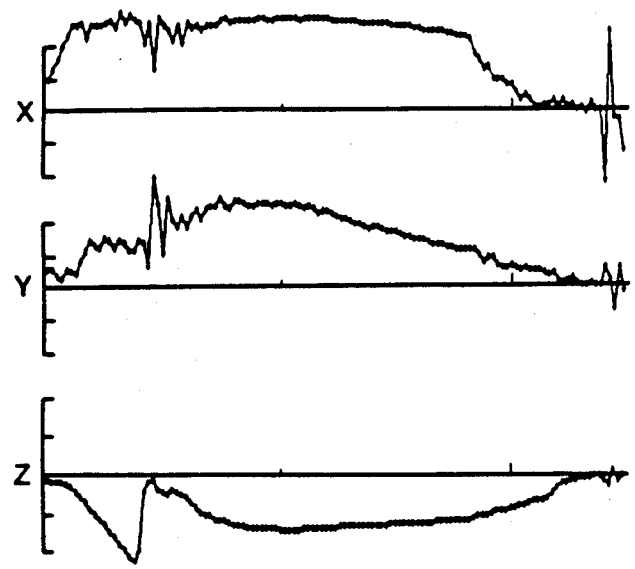
FIG. 7a shows a graph of the x, y, and z forces as a function of time for one successful assembly of the part.
Figure 7B:
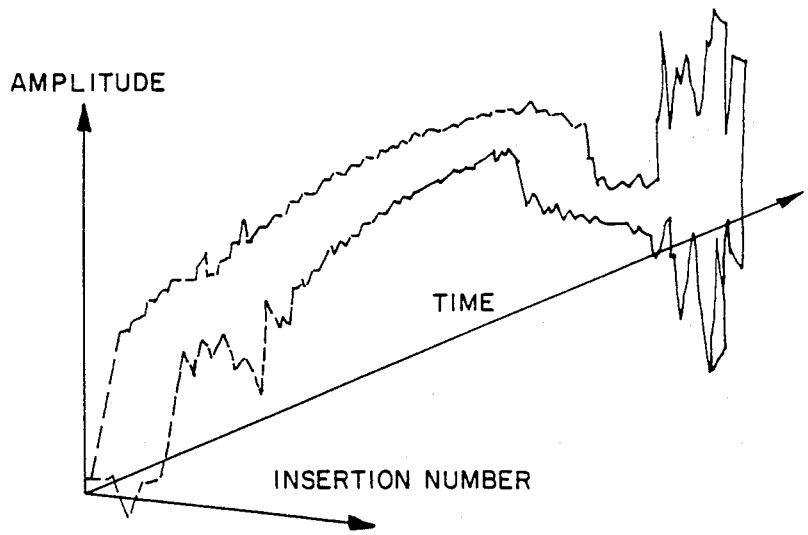
FIG. 7b shows the x forces as a function of time for a plurality of good assemblies of the part.
Figure 7C:
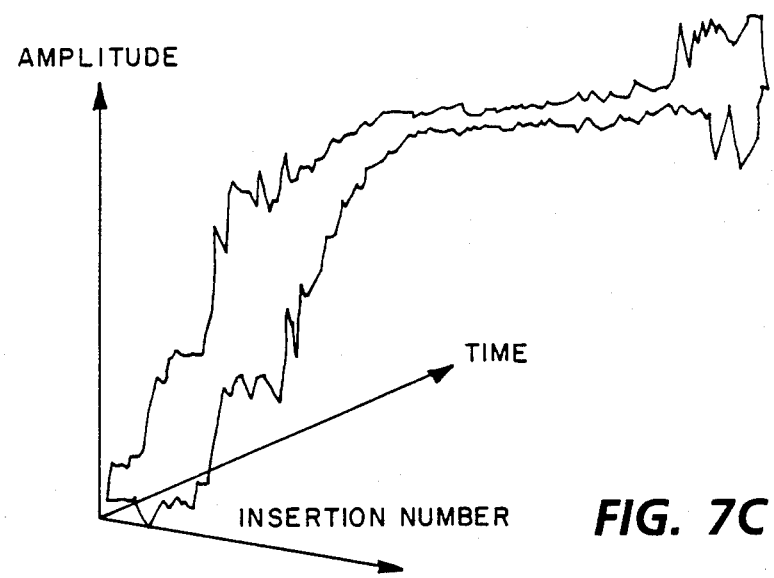
FIG. 7c shows the y forces as a function of time for a plurality of good assemblies of the part.
Figure 7D:
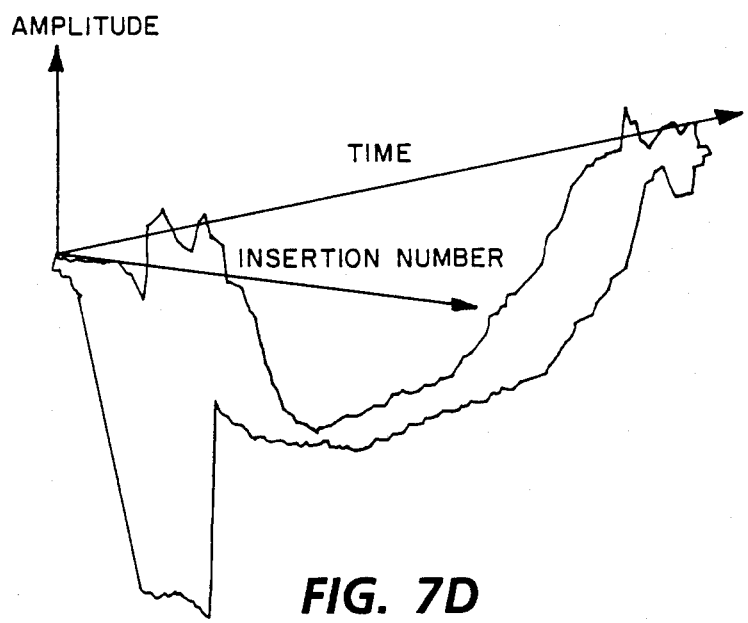
FIG. 7d shows the z forces as a function of time for a plurality of good assemblies of the part.
Figure 9A:
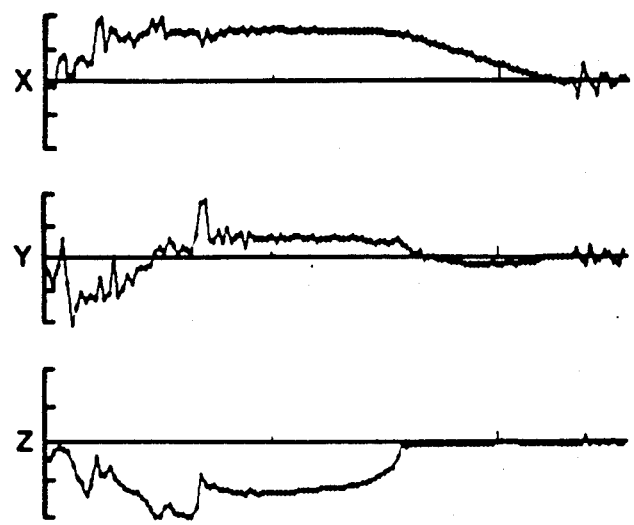
FIG. 9a shows a graph of the x, y, and z forces as a function of time when the part is in the end effector gripper backwards.
Figure 9B:
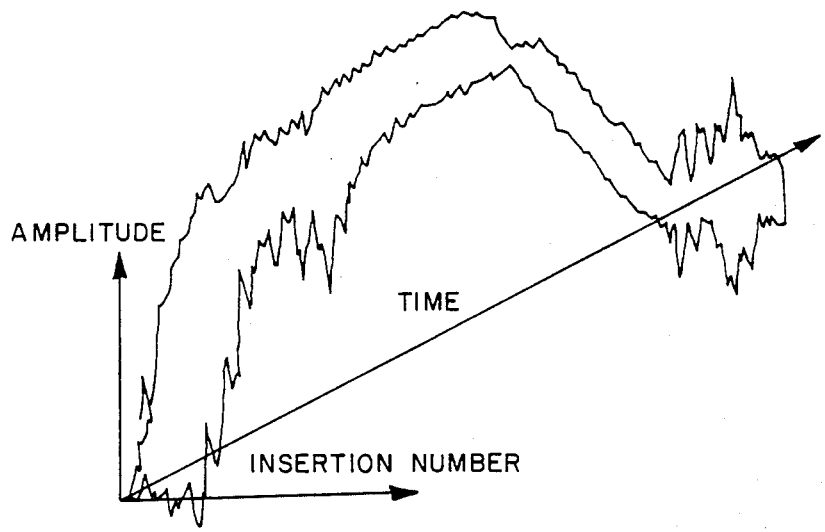
FIG. 9b shows the x forces as a function of time for a plurality of assemblies when the part is in the end effector gripper backwards.
Figure 9C:
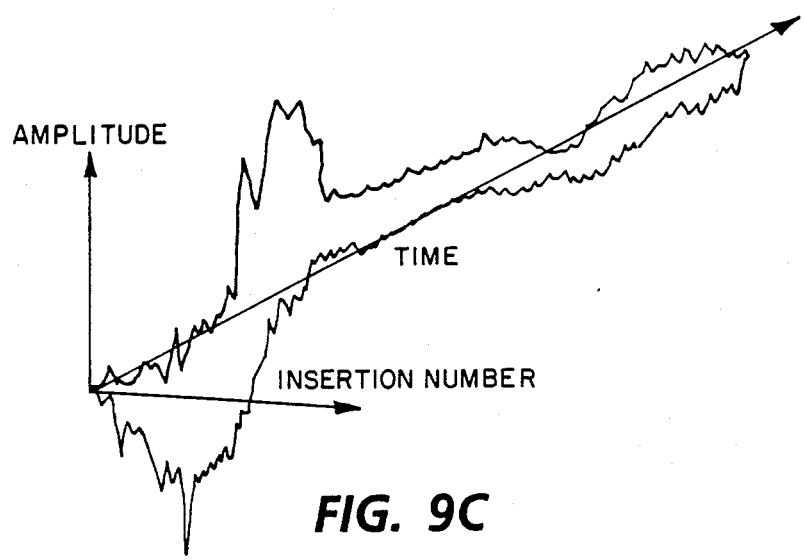
FIG. 9c shows the y forces as a function of time for a plurality of assemblies when the part is in the end effector gripper backwards.
Figure 9D:
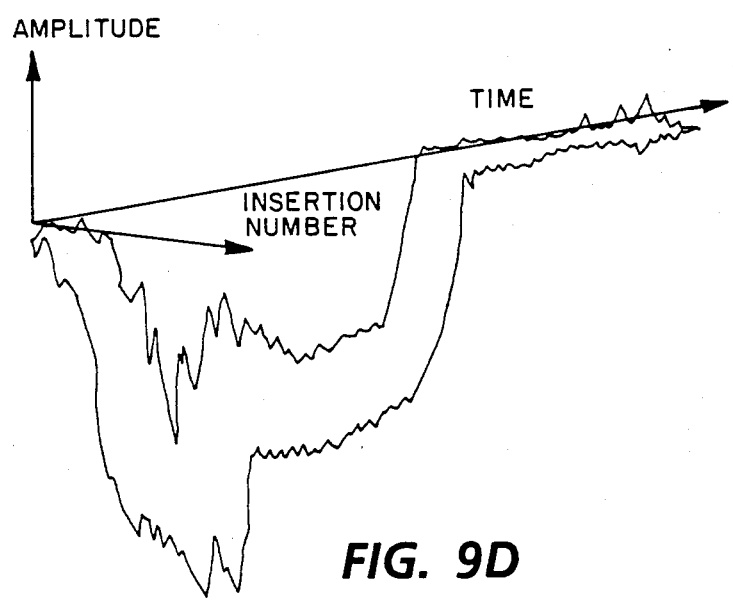
FIG. 9d shows the z forces as a function of time for a plurality of assemblies when the part is in the end effector gripper backwards.
Figure 10A:
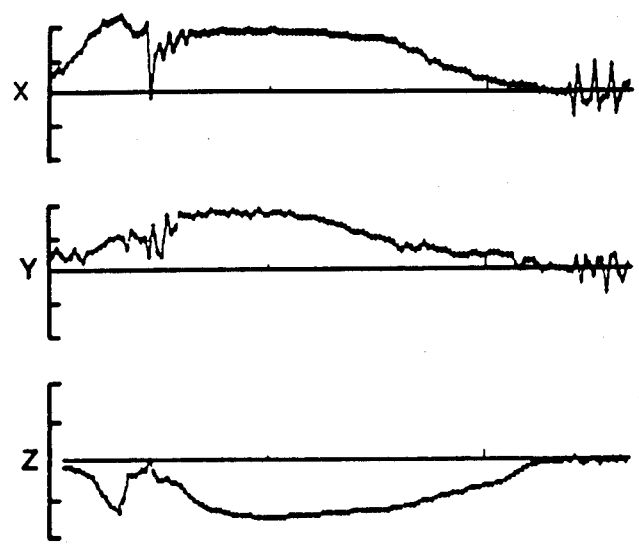
FIG. 10a shows a graph of the x, y, and z forces as a function of time when a portion of the part is missing.
Figure 10B:
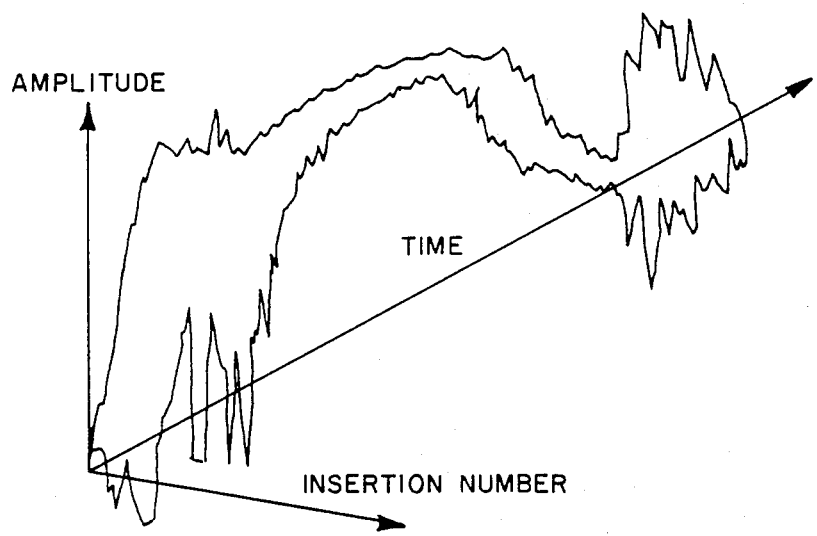
FIG. 10b shows the x forces as a function of time for a plurality of assemblies when one portion of the part is missing.
Figure 10C:
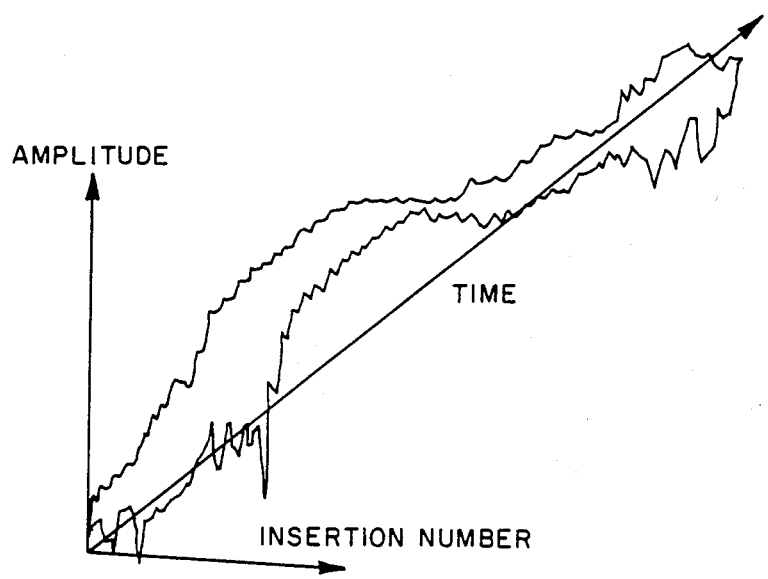
FIG. 10c shows the y forces as a function of time for a plurality of assemblies when one portion of the part is missing.
Figure 10D:
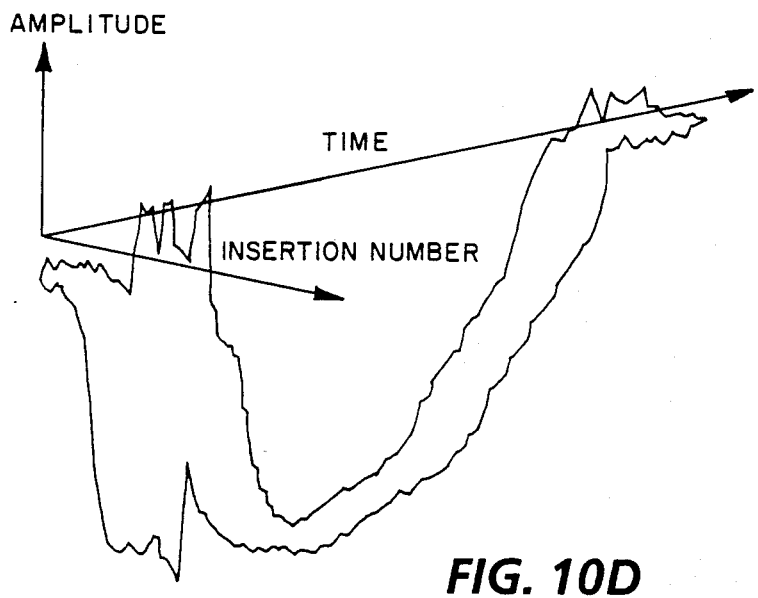
FIG. 10d shows the z forces as a function of time for a plurality of assemblies when one portion of the part is missing.
Figure 11A:
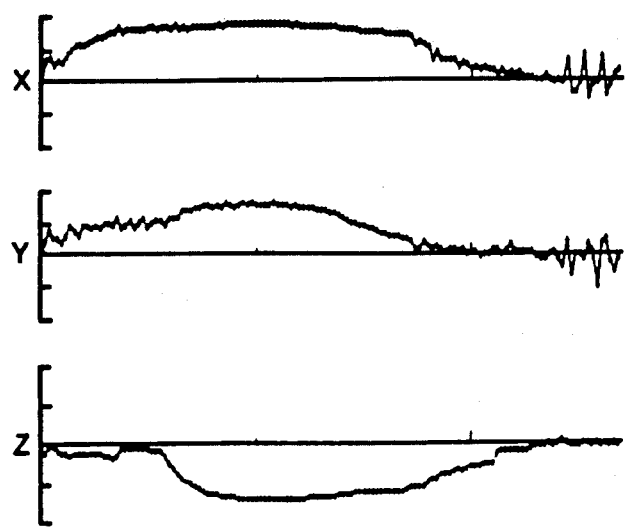
FIG. 11a shows a graph of the x, y, and z forces as a function of time when two portions of the part are missing.
Figure 11B:
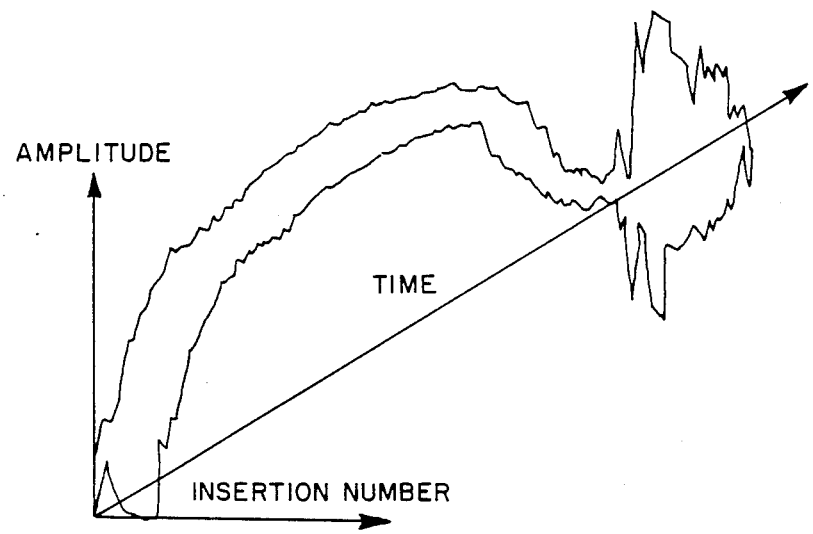
FIG. 11b shows the x forces as a function of time for a plurality of assemblies when two portions of the part are missing.
Figure 11C:
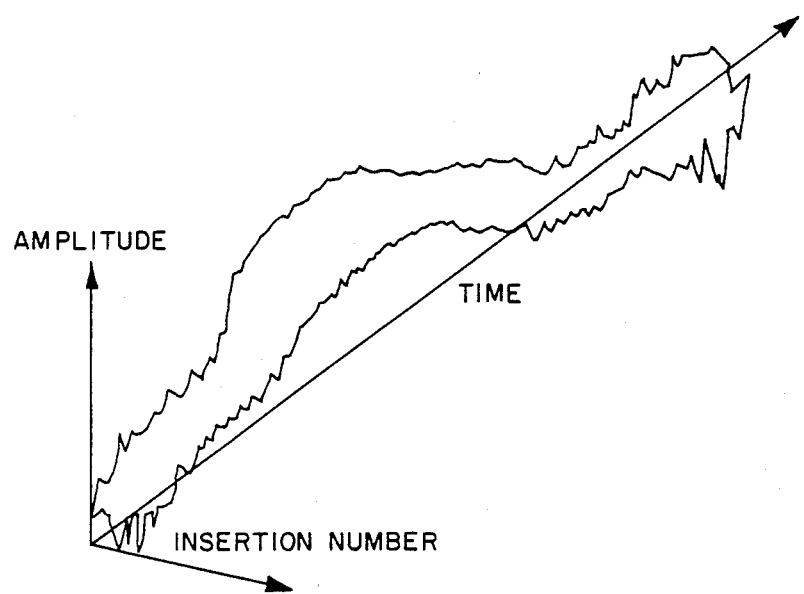
FIG. 11c shows the y forces as a function of time for a plurality of assemblies when two portions of the part are missing.
Figure 11D:
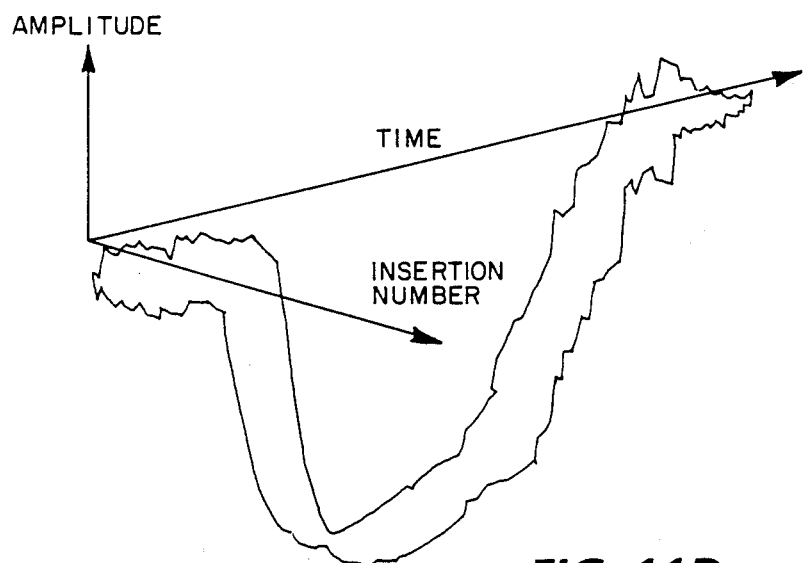
FIG. 11d shows the z forces as a function of time for a plurality of assemblies when two portions of the part are missing.
Figure 12A:
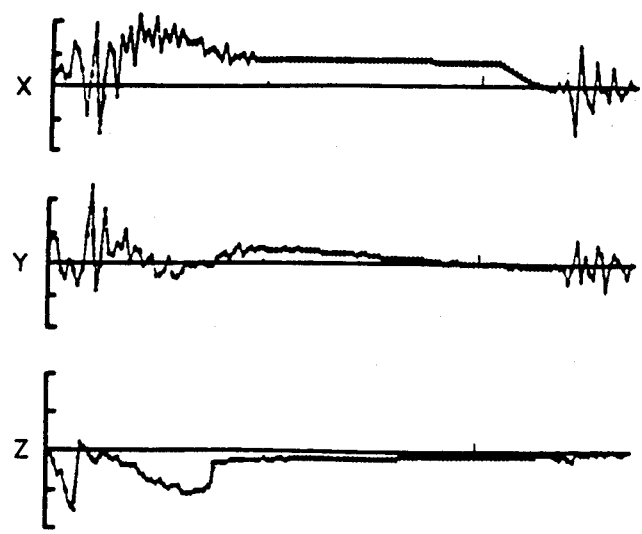
FIG. 12a shows a graph of the x, y, and z forces as a function of time when the wrong part is being assembled.
Figure 12B:
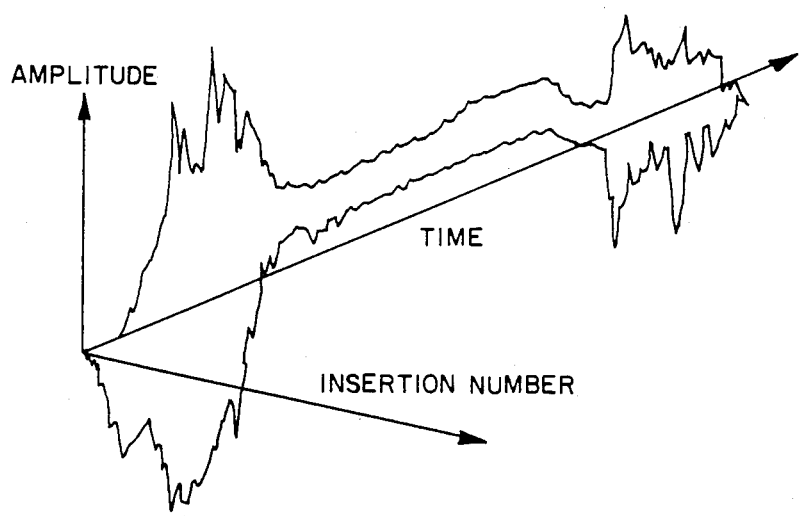
FIG. 12b shows the x forces as a function of time for a plurality of assemblies when the wrong part is being assembled.
Figure 12C:
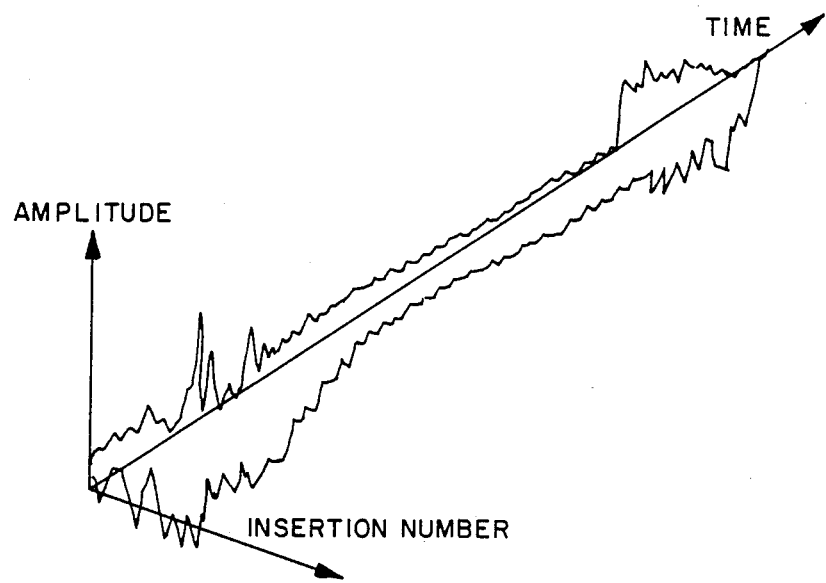
FIG. 12c shows the y forces as a function of time for a plurality of assemblies when the wrong part is being assembled.
Figure 12D:
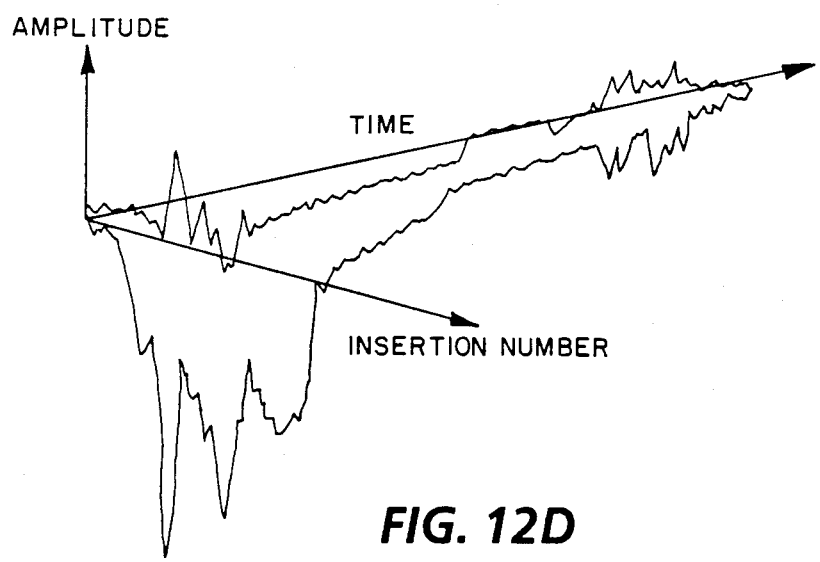
FIG. 12d shows the z forces as a function of time for a plurality of assemblies when the wrong part is being assembled.
Figure 13A:
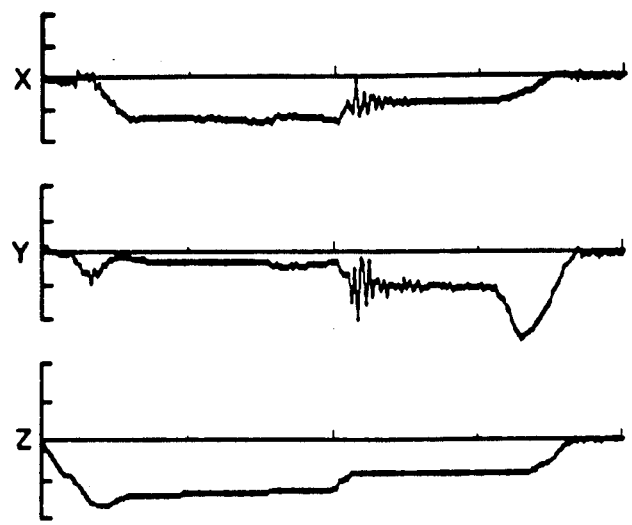
FIG. 13a shows a graph of the x, y, and z forces as a function of time when the parts being assembled collide with one another.
Figure 13B:
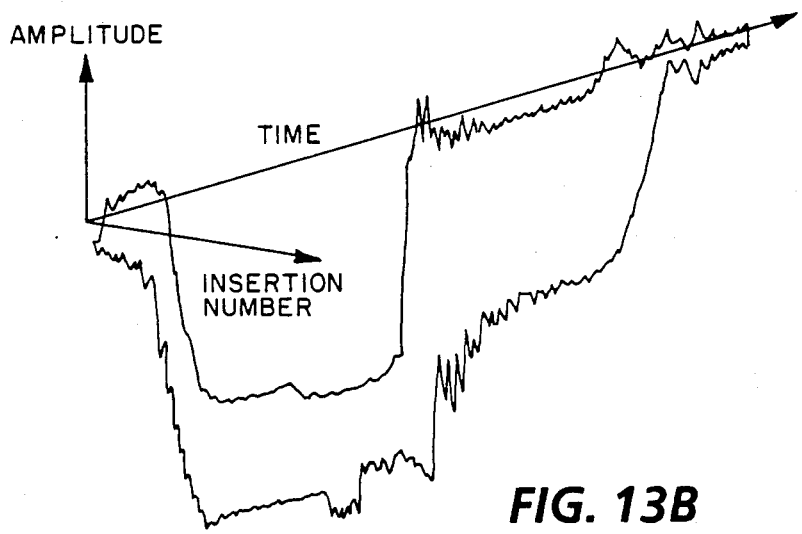
FIG. 13b shows the x forces as a function of time for a plurality of assemblies when the parts being assembled collide with one another.
Figure 13C:
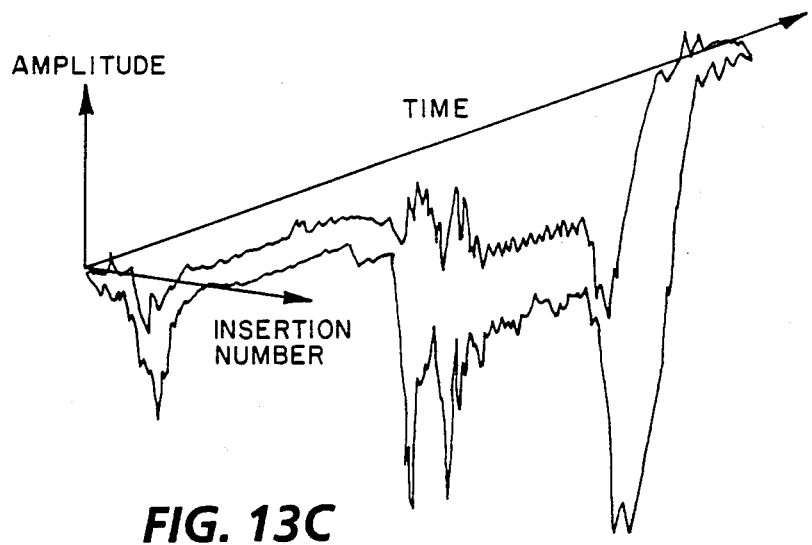
FIG. 13c shows the y forces as a function of time for a plurality of assemblies when the parts being assembled collide with one another.
Figure 13D:
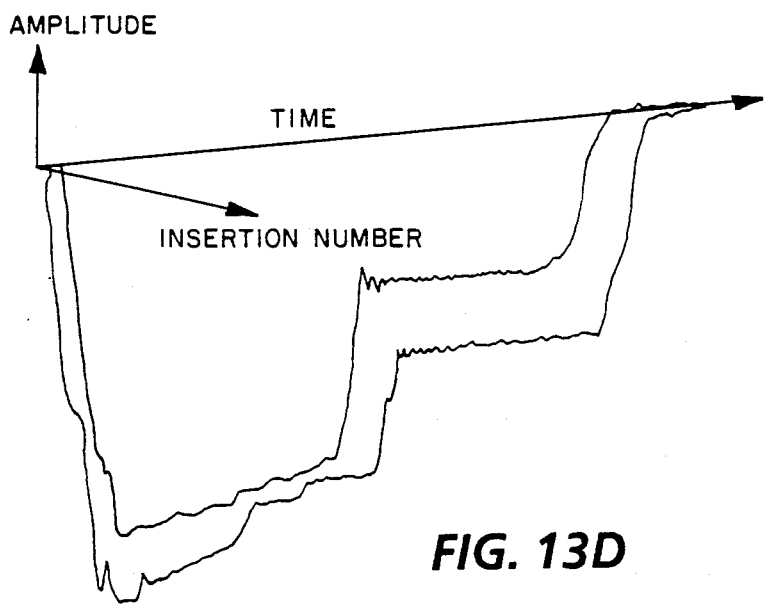
FIG. 13d shows the z forces as a function of time for a plurality of assemblies when the parts being assembled collide with one another.

The forces required to assemble two parts are directly related to the parts themselves and to the process which joins them together. The process used to record force information begins when the part is picked up and continues until the switch is fully inserted into the frame during a vertical insertion. FIG. 6 shows the forces acting along the x, y and z axes of the sensor during a successful insertion of the switch into the mock frame. The plots are shown positive downward. The forces remain at zero until the two parts contact. Upon initial contact, all three force waveforms indicate that x, y and z forces are being applied to the sensor. As the switch is pushed further into the frame, an alignment occurs in which the part and frame are aligning relative to themselves. The x and y plots show that the parts are experiencing some alignment forces. This alignment can be translational or rotational depending on the relative starting positions of the two parts. The z-axis shows a large spike due to the actuation of the snap feature on the switch. The snap feature is designed to be a cantelever beam deflection, which requires more force to deflect as it is pushed into the frame. At the point of the snap action, the Z force drops off close to zero. At this point, the X and Y forces indicate some form of sinusoidal shock wave. The shock wave would be more clearly shown at a higher sampling speed. This shock wave is due to the actuation of the snap exciting the mechanical resonance of the system. After the snap actuation, the robot is programmed to continue pushing the parts together until a certain vertical dimension is reached, a point where the switch is lightly pressing against the frame. At this point, the three force traces indicate that the forces rise to some maximum value and remain for a time. When the gripper opens, the forces relax as the part clears the gripper fingers. As this particular gripper opens to full width, the fingers hit hard stops. This creates a shock wave through the gripper and is sensed by the force sensor. The shock wave is distinguishable on all three waveforms. As more signals are collected with the same setup, the forces along all three axes are seen to be very similar. FIG. 7a shows the x, y, z forces in two dimensions for one particular waveform. FIGS. 7b, 7c and 7d show the envelope or bandwidth of a three dimensional plot of a series of the x, y, z forces plotted side-by-side for the same group. The similarity of these plots allows the use of statistical classification techniques.

There are several different ways in which the snap switch may be assembled incorrectly. For example, (1) no part in the gripper; (2) the part might be put in the packaging backwards and grasped incorrectly; (3) one or both of the snap features on the switch are broken off; (4) the wrong part was picked up; and (5) the switch and the frame are grossly misaligned.

FIG. 8 shows the force profile of a situation where there is no part in the gripper to assemble to the frame. There is no initial contact force. In fact, the only force indicated is the shock wave of the gripper opening.

FIGS. 9a through 9d, inclusive, show the waveforms corresponding to FIGS. 7a through 7d, inclusive, where the part is positioned backwards within the gripper. This particular situation can occur when the part to be inserted is symmetric with respect to the pick up points on the robot. In fact, this switch was frequently inserted backwards into the product because of confusion about the correct orientation of the part within the packaging. No matter how the switch was oriented in the package, the robot would still be able to pick up and place it into the final product. Undetected, this would cause a definite functionality problem later in the assembly process. The mispositioning of the switch in the gripper produces a substantially different force profile during assembly. These differences are due to a new set of complying forces along the x and y axes. In addition, the snap spike does not have the clean triangular shape of the "good" waveform. This is caused by the switch not being inserted truly perpendicular to the frame, hence, not allowing the proper snap action.

An additional problem is where one of the snap features of the switch is broken off. Such a condition results in the switch not being properly secured in the frame and will eventually cause a functionality problem. FIGS. 10a through 10d, inclusive, show the waveforms corresponding to FIGS. 7a through 7d, inclusive, where one of the snap features of the switch is broken off. The force profile is different from the "good" force profile in that the forces along the x and y axes are decidedly different especially on the x-axis.

FIGS. 11a through 11d, inclusive, show the waveforms corresponding to FIGS. 7a through 7d, inclusive, where both of the snap features of the switch are broken off. With both legs missing, there is no spike caused by the actuation of the snap.

Under certain conditions, a similar but wrong part might be inserted into the assembly. For example, parts from a different vendor may have substantially different functions, but may be sufficiently similar to be loaded into the assembly system. Frequently, this situation is not detected until after the product is built. To simulate this condition, a switch with similar snap features and pick positions was fabricated. The resulting force profile is shown in FIGS. 12a through 12d, inclusive. The force profile is substantially different in almost all segments of the force plot.

Parts colliding is the most commonly occurring problem during assembly. This is caused by misalignment of the part to the product caused, in turn, either by the robot mispositioning the part or the conveyor system not positioning the product accurately. This condition was simulated by mispositioning the product under the robot in such a manner that the switch would not line up over the holes. As the robot pushed the switch into the frame, the switch and frame collide. FIGS. 13a through 13d, inclusive, show the waveforms corresponding to FIGS. 7a through 7d, inclusive, where the switch collides with the frame. The resulting force profile indicates extreme z-forces.

To classify the waveforms, a feature extraction occurs on the force profiles. Weight, extreme maximum and minimum threshold values are used for force control. The weight feature is calculated by averaging the z-force before the part is placed, and subtracting this value from the averaged z-force after the part is placed. The averaging is performed to reduce noise in the system. It is given by:

$$W = \frac{\sum_{i=b-l}^{b} F_z i - \sum_{i=a}^{a+l} F_z i}{l},$$

where:
W=weight,
l=length of time over which to average weight,
a=time at beginning,
b=time at end,
$F_z i = Z$ force at time i, and
$F_z a \leq F_z i \leq F_z b$, The weight feature is easy to compute. However, it is limited to measuring part weights that are within the specifications of the sensor. With the switch, in particular, there is a condition where the magnet might not have been inserted into the switch before it was inserted into the frame. The weight of the magnet is small relative to the resolution of the force sensor so that its absence goes undetected.

Extreme maximum and minimum force threshold values is frequently used for detection of contact between parts; either for crash detection or for "finding" parts in the work space, i.e., the robot is commanded to move until it "touches" the part. This scanning routine locates parts whose locations are not precisely known.

A measure of the energy imparted during an impact between two rigid bodies is the the linear impulse of the force. It provides information on the amount of energy imparted during the assembly. It is equivalent to integrating the area under the instantaneous force curve with respect to time and can be estimated with an application of Simpson's rule given by:

$$\Sigma \frac{3}{8} h (F_1 + 3F_2 + 3F_3 + 2F_4 + 3F_5 + \ldots + 2F_{n-2} + 3F_{n-1} + 3F_n + F_{n+1}),$$

where:
$F_n$ is a discrete force sample and h is the time between $F_n$ and $F_{n+1}$.

A computationally simple method to determine if two signals are similar is to integrate the absolute difference between them. This may be determined by:

$$D = \frac{\sum_{i=a}^{b} |F_i - F_{Ti}|}{b - a},$$

where:
$F_i$=unknown force at time i,
$F_{Ti}$=template force at time i,
a=starting time, and
b=ending time.

Autocorrelation provides a measure of the strength of the signal—a measure of its nonrandomness. Signals having a strong structure exhibit a slowly changing autocorrelation about the zero-lag value and decay rapidly. The autocorrelation feature was used to determine the structure of the insertion waveform, at a single lag value arbitrarily chosen to be equal to 1. It is computed by:

$$\frac{\sum_{i=a}^{b-1} (F_i * F_{i+l})}{b - a},$$

where:
l=lag.

Cross correlation provides information about the similarity between two signals. It is computed by:

$$\sum_{i=a}^{b} \frac{(F_i * F_{T(i-l)})}{b - a}$$

where:
F=signal being processed
$F_T$=reference signal, and
l=lag.

The lag chosen for this calculation is zero. This will compare the two signals on a point-by-point basis as they superimpose upon each other and provide a single value output.

To calculate the features of waveforms, the good signals must first be averaged for use with the integral of the difference and the cross correlation function. This is accomplished by the program called AVERAGE. With the averaged "good" signal now available, the program "FEATURE" is run. Once the features have been calculated for all the waveforms, the operator must collect the signals into groups and identify them to the system. This is accomplished by running the MANOVA program which computes the multivariate analysis of variance of each of the groups of waveforms. The operator begins by defining each of the different types of waveforms to be classified. For example: no part, missing one leg, missing both legs, etc.. As each group is defined, the program requests information on the name of each of the feature data files which make up the groups. The execution of this program creates a dispersion matrix which is used to classify future unknown signals in the classification program.

To help in the logistics of location of the data file, a program called MAKEDATA is executed. It collects the location information of the data files and stores it in a file. After the MAKEDATA program has been executed, the MANOVA program uses the location information and feature selections to create the dispersion matrix.

To this point, all of the learning of the system has been accomplished. It is now possible to begin to classify unknown waveforms against the learning set. This is accomplished by running the WRISTCOM program to obtain the new waveform. The Convert program then converts data to real values, and the Feature program creates a feature set from the waveform. At this point, the waveform can be classified against the learned waveforms.

To classify a waveform, the user selects the CLASSIFY option and identifies the group number to which the waveform belongs. This is used to calculate hit/miss ratios, Hit, of correct classifications. After a group number is defined, the waveform file is requested. After entering the file name, the program calculates the classification statistic, and plots the data on the screen.

Four experiments were performed with the system: (1) developing a feature set to classify insertion waveforms of the snap switch; (2) testing the developed feature set by classifying previously untrained insertion waveforms; (3) identifying waveforms which were or were not part of the trained groups; and (4) retraining the system to classify waveforms of parts picked from packaging rather than being placed in a product.

The first experiment identified a set of features that provided the highest classification accuracy of the placement of the switch. A set of waveforms of possible ways in which the switch may be inserted was collected. The system was then trained using these waveforms. The training set waveforms were then classified while the feature set was varied to determine the set of features which provide the highest classification accuracy. The waveforms used in all of the experiments were obtained by running the WRISTCOM and CONVERT programs as previously discussed. There were forty six good and thirty six bad insertion waveforms collected. There were twenty four good insertions using the same switch, and twenty two good insertions using different switches. There were six ways to achieve a bad insertion; (1) no part in the gripper, (2) the part picked up backward, (3) one of the snaps missing, (4) both of the snaps missing, (5) the wrong switch inserted, and finally (6) a crash condition. In each of these six cases, six waveforms were collected; the total was thirty six. After obtaining the waveforms, the system was trained to recognize each of these groups by running the AVERAGE, MAKEDATA, and MANOVA programs. The averaged waveform eventually was defined by averaging eleven waveforms of different switch insertions and twelve waveforms of repeated insertions of the same switch. Some experimentation was required to arrive at the set of waveforms to be used to calculate the averaged waveform. Initially, all twenty-two of the varied switch placements were used to calculate the averaged waveform. Upon training the system to classify the varied switch placements as good insertions, the multiple insertions of the same switch classified poorly. Upon investigation, it was found that these two waveforms classes were sufficiently different to be classified as two distinct groups. This disparity was a result of a difference in instrumentation setup. Rather than rescheduling additional time to collect more data, it was decided to consider both groups as being good insertions and to group them together for the classification. This is not an extremely poor assumption since the waveforms are very similar in appearance and are only slightly different in the feature sets. Using this assumption, the averaged waveform was defined. The number of waveforms to be averaged together was arrived at by observing the averaged waveform derived from n waveforms. A sufficient quantity of waveforms were selected to be a good representative sample of the population, but not too much or features of the waveform would be attenuated. In averaging twenty four signals together it became apparent that the spike due to the snap was being rounded off. Using these two rules as guidelines, it was found that twelve waveforms would suffice. The quantities of waveform samples were arrived at arbitrarily. No analytical work was done to identify the optimal number of insertion waveforms required during the training set. It appears that the features are normally distributed. This is in agreement with the underlying assumption upon which the maximum likelihood classifier is based. All of the seventy nine waveforms available were used during the learning set, and were also later classified. The x, y and z options were all selected for each feature function during the MADEDATA program and were used in the classification. The classification of the respective waveform to a group was determined by choosing the group in which the unknown waveform had the highest probability of membership. The use of the max and min features show a definite tendency of not being able to provide accurate classification to the defined groups. In each case where max and min were used, the classification Hit percentage was no greater than sixty six. This is to be expected since max and min tests are currently used for detection of crashes and lack of part, and not for all of the possible error conditions tested for in this experiment. By using max and min only, the classification technique clearly detects the absence of the part from the gripper; however classification of crashes, backwards parts, etc. are not accurate. Adding more features to the feature set does not necessarily improve the classification accuracy. For example, when all the possible features are included in the feature set, the Hit percent is only four. Therefore, an optimal feature set which is neither too large nor too small must be selected. The feature set which provided the greatest accuracy on this test data included all of the possible features with the exception of max and min. The Hit percent was 100. In fact, the classification provided very distinct results. The calculated probability of correct group membership is 99% in only two instances. From the results, it was determined that the feature set to be used for future classifications of placing the switch should consist of the x, y and z values associated with the Integral of the Difference, Impulse, Autocorrelation and Correlation functions. After a feature set was found which enabled the highest correct prediction rate, the learning set was reduced to be able to classify waveforms which had not been used during the learning set. A sufficient number of waveforms were used in the training set to provide a statistically representative sample upon which to define groups. After a few iterations of potential learning sets, a set was found which provided 100% correct classifications of the unknown and known waveforms. The learning set consisted of thirty six waveforms. A feature set was found which classified the insertion waveforms for this particular snap switch and had an accuracy of prediction greater than 90%. In the event a waveform does not belong to any of the learned groups, the classification system must indicate that the waveform is unrecognizable. An experiment was then performed where waveforms from the picking of the switch were classified against waveforms of the switch being placed. In each case where the unknown waveform was classified, the absolute probability of membership in groups defined during placing of the switch was extremely small $<10^{-30}$. This would indicate that a simple threshold may be used to indicate if the waveform is recognized to belong to a trained group or not. Classification of pick waveforms was done in addition to classification of the placement of the switch. The waveforms were obtained and classified in a similar manner. However, it was found that the performance of the system was extremely poor. This led to experimentation to determine a feature set which would provide the highest classification performance. Indeed, a new set of features must be selected to accurately classify the pick waveforms. Apparently any three features selected (with the exception of Max, Min and weight) would provide satisfactory response. Max and min were not used in this exercise since they performed so poorly in the previous experiment.

The computer program listings for the various programs discussed hereinbefore may be found in the appendix.

In recapitulation, the system of the present invention is trained to classify the assembly waveforms into good and bad waveforms corresponding to good and bad assembly operations. During assembly, the actual waveforms are compared to the previously identified waveforms. If the actual waveforms is a good waveform, the part is accepted. Contrawise, if the actual waveform is determined to be a bad waveform, the part is rejected.

It is, therefore, evident that there has been provided, in accordance with the present invention, a system that fully satisfies the aims and advantages hereinbefore set forth. While this invention has been described in conjunction with a preferred embodiment and method of use thereof, it is evident that many alternatives, modifications, and variations will be apparent to those skilled in the art. Accordingly, it is intended to embrace all such alternatives, modifications and variations as fall within the spirit and broad scope of the appended claims.

I claim:

1. A method of assembling parts, including the steps of:
    sensing, at discrete time intervals before actual assembly of the parts, forces exerted on the parts corresponding to a good assembly and a faulty assembly;
    processing statistically the sensed forces to determine waveforms corresponding to the forces associated with a good assembly and the forces associated with a faulty assembly;
    detecting, at discrete time intervals, forces exerted on the parts during the actual assembly of the parts;
    processing statistically the detected forces to determine waveforms of the forces used during actual assembly of the parts;
    comparing the waveforms of the forces used during actual assembly of the parts to the waveforms corresponding to the forces associated with a good assembly and a faulty assembly to classify the waveforms of the forces used during actual assembly of the parts as those associated with a good assembly or those associated with a faulty assembly.

2. A method according to claim 1, wherein said step of processing the sensed forces includes the step of employing a maximum likelihood statistical technique to form the waveforms corresponding to the forces associated with a good assembly and the forces associated with a faulty assembly.

3. A method according to claim 2, wherein said step of processing the detected forces includes the step of employing a maximum likelihood statistical technique to form the waveform of the actual forces used during assembly of the parts.

4. A method according to claim 3, further including the step of assembling the parts with an assembly robot having an end effector for holding the parts with a plurality of degrees of motion.

5. A method according to claim 4, wherein said step of processing statistically the sensed forces and said step of processing statistically the detected forces includes the step of using a computer to perform the required computations.

* * * * *